United States Patent [19]

Lundin et al.

[11] 4,235,772
[45] Nov. 25, 1980

[54] NOVEL PEPTIDES HAVING GROWTH PROMOTING ACTIVITY

[75] Inventors: Ronny-Hugo L. Lundin, Johanneshov; Gertrud E. Westin-Sjödahl, Södertälje; Karin H. L. Bergendal, Danderyd; Linda M. Fryklund, Kungsängen, all of Sweden

[73] Assignee: AB Kabi, Stockholm, Sweden

[21] Appl. No.: 50,962

[22] Filed: Jun. 20, 1979

[30] Foreign Application Priority Data

Jun. 21, 1978 [SE] Sweden ................................ 7807114

[51] Int. Cl.³ ...................... C07C 103/52; C12N 5/00; C12N 5/02
[52] U.S. Cl. .............................. 260/112.5 R; 435/240; 435/241
[58] Field of Search .............................. 435/240, 241; 260/112.5 R

[56] References Cited

U.S. PATENT DOCUMENTS 4,058,512  11/1977  Sievertsson et al. ......... 260/112.5 R Primary Examiner—Delbert R. Phillips
Attorney, Agent, or Firm—A. A. Orlinger

[57] ABSTRACT

Described are novel growth promoting peptides of the general formula:

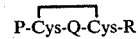

P-Cys-Q-Cys-R where
P is hydrogen, or Phe-Asn-Val-Asp-Lys-Lys-;
Q is selected from -Gln-, or -Ser-Tyr-Tyr-Gln-Ser-Asn-, or -Tyr-Thr-Ala-Glu-; and
R is selected from -Thr, -Lys-Pro-Gln-Val-Thr, or -Asp-Glu-Leu;

and of the corresponding reduced linear form of any of the foregoing, as well as the corresponding pharmaceutically acceptable acid addition salts of any of the foregoing. The corresponding intermediates or intermediary compounds with amino and/or carboxyl groups protected are also covered.

9 Claims, No Drawings

NOVEL PEPTIDES HAVING GROWTH PROMOTING ACTIVITY

The present invention relates to novel peptides having growth promoting activity and the general formula (I):

and the corresponding reduced linear form of any of them, and wherein

P is hydrogen, or Phe-Asn-Val-Asp-Lys-Lys-;
Q is selected from -Gln-, or -Ser-Tyr-Tyr-Gln-Ser-Asn-, or -Tyr-Thr-Ala-Glu-; and
R is selected from -Thr, -Lys-Pro-Gln-Val-Thr, or -Asp-Glu-Leu;

and the corresponding peptides in which the reactive groups (i.e. amino and/or carboxyl) are protected on any of Asp, Cys, Glu, Lys, Ser, Thr or Tyr, as well as the pharmaceutically acceptable acid addition salts of any of the foregoing.

The amino acids of formula (I) as well as any of their pharmaceutically acceptable corresponding acid addition salts may be present in their L-form or in their D-form, and the compounds of formula (I).

The acid addition salts are readily obtained by methods known in the art of peptide synthesis.

The present invention also comprises methods for preparing the novel peptide compounds of formula (I). These compounds can be prepared by any of the methods which are well known for the preparation of this kind of compound or by means of any corresponding chemically equivalent method. The compound, for example, can be prepared as follows:

1. by joining two peptide units, each containing at least one amino acid in protected or unprotected form, by means of an amide group linkage, and then, if necessary, removing any protecting groups, the peptide units being selected or built up and linked together in such a manner that the amino acid sequence indicated in formula (I) is provided;
2. by removing at least one protecting group which is present in a protected polypeptide having the sequence of amino acids indicated in formula (I); or
3. by oxidizing a (reduced) linear compound corresponding to formula (I) to obtain the cyclic compound of formula (I).

The above mentioned methods are, as such, well known in the art of peptide chemistry, and the starting materials used (e.g. amino acids and/or peptides) are readily available or readily can be produced and purified by known methods.

According to a preferred embodiment of the invention the peptides of formula (I) are prepared by means of solid phase peptide synthesis. This synthesis preferably is started from the C-terminal end by attaching the desired amino acid (or peptide fragment) to a solid carrier capable of reversibly binding amino acids. Before attaching the amino acid (or peptide fragment) to the carrier, the α-amino group and possible side chain groups are protected by suitable protecting groups. After the coupling of the protected amino acid (or peptide) to the carrier, the α-amino protecting group is removed by means of an agent which does not affect the carrier-amino acid bond. The remaining amino acids are then attached stepwise in the desired order (one by one or in the form of di- or polypeptides) until the desired sequence of amino acids given by formula (I) has been provided. The peptide formed is then removed from the carrier by treatment with an agent which preferably does not only cleave the peptides from the carrier, but also splits off all or most of the remaining side chain protecting groups.

Preferred carriers or supports are chloromethylated polystyrene resins cross-linked with 1 to 2% of divinylbenzene (commercially available from, e.g., Bio-Rad Laboratories Richmond California, U.S.A.). The preferred agents for splitting off the polypeptide formed from the carrier are hydrogen fluoride in the presence of anisole, and a mixture of hydrobromic acid and trifluoro acetic acid.

The solid phase synthesis technique discussed above is well known in the art, see, e.g., Merrifield, J.Am.-Chem.Soc., 85, p. 2149 (1964); Stewart et al. "Solid Phase Peptide Synthesis", Chapter 1, pp. 1–6 (Freeman & Co., San Francisco (1969); Monahan & Gilen, Biopolymer, 12, pp. 2513–19 (1973).

The peptides of formula (I) also can be synthetized in solution by stepwise coupling of the amino group of one amino acid with the carboxyl group of another amino acid to form the usual amide linkage. The amino (or carboxyl) group of the new peptide fragment obtained then is coupled to the carboxyl (or amino) group of another amino acid, and the procedure is repeated until the desired sequence of amino acids, i.e., the selected polypeptide of formula (I), has been formed. The synthesis, for example, may be started at the N-terminal or at the C-terminal.

The invention is not restricted to adding only one amino acid in each step, but it is also possible to combine peptide fragments, each corresponding to a certain part of the desired peptide of formula (I). For example, a tridecapeptide of formula (I) can be prepared by coupling a suitable undecapeptide with a suitable dipeptide, or a suitable decapeptide with a suitable tripeptide, and so on. The amino acids and smaller peptide fragments can be used in their unprotected form, but those of their functional groups which are not intended to take part in the respective coupling reactions, are blocked preferably by means of suitable reactive groups, as is well known in the art. The formation of the respective amine linkages preferably is promoted, for example, by using activated esters, such as a 2,4,5-trichlorophenyl ester, a pentachlorophenyl ester, a p-nitrophenyl ester, or adding a suitable coupling agent such as N,N'-dicyclohexyl carbodiimide.

The preferred amino protecting group is tert-butyloxycarbonyl, and other non-limiting examples of suitable protective groups for blocking an amino group are formyl, trifluoroacetyl, phthalyl, toluenesulfonyl, benzenesulfonyl, nitrophenylsulfenyl, tritylsulfenyl, o-nitrophenoxyacetyl, chloroacetyl, acetyl, y-chlorobutyryl, benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl, diisopropylmethoxycarbonyl, isopropyloxycarbonyl, ethoxycarbonyl, allyloxycarbonyl, cyclopentyloxycarbonyl, adamantyloxycarbonyl, cyclohexyloxycarbonyl, phenylthiocarbonyl, trityl, benzyl. The —COOH groups can, for example, be protected by means of salt or ester or hydrazide formation, suitable esters being, e.g. the methyl, ethyl, benzyl, t-butyl esters. Some of the amino acids may also require protection of reactive side chain groups.

Illustrative of suitable side chain amino protective groups are benzyl, bromobenzyloxycarbonyl, benzyloxycarbonyl, tosyl, t-amyloxycarbonyl, t-butylyoxycarbonyl, etc. The selection of such a side chain amino protecting group is not critical except that it must be one which is one removed during deprotection of the α-amino groups during the synthesis.

Hence, the α-amino protecting and side chain amino protecting group cannot be the same. A protecting group for Cys can be selected from the group consisting of S-p-methoxybenzyl, S-p-methylbenzyl, S-acetamidomethyl, S-trityl, S-benzyl, and the like. Protecting groups for the hydroxyl group of Thr and Ser can be selected from the groups consisting of acetyl, benzyl, tert-butyl, trityl, tetrahydropyranyl, benzyl, 2,6-dichlorobenzyl and benzyloxycarbonyl. The preferred group is benzyl. The protecting groups can be split off in a manner known per se, for example, by means of acid or alkaline hydrolysis, by catalytic hydrogenation, by using sodium in liquid ammonia, by Hg(II), etc., depending on the nature of the protecting groups and the reactants used.

Linear peptides corresponding to formula (I) can be converted into the corresponding cyclic peptides by treatment with a mild oxidizing agent which does not affect other oxidizable groups in the molecule. Examples of suitable oxidizing agents are air, oxygen, potassium ferricyanide, iodine and the like. The oxidation is preferably carried out in a buffer at a pH ranging from about 6.5 to 7.5, in particular about 7.2.

The new peptides of formula (I) exhibit interesting cell growth promoting properties, i.e., they stimulate the growth of cells originating from mammalian, for example, human, tissue. Thus, in vitro tests on cell cultures of human embryonic lung fibroblasts have demonstrated that the new peptides of formula (I) cause a considerable increase in the cell growth. This test, which illustrates that the whole cell cycle proceeds normally and is stimulated by the peptides of formula (I), is indicative of physiological as well as pharmacodynamic activity, and suggest that the compounds may be used as drugs for treating humans or animals in order to promote cell growth, e.g., for accelerating the healing process of burns or after surgery. The peptides of formula (I) also can be used as an agent for enhancing the production of medically important cell substances such as vaccines, interferons, and other mammalian tissue cells produced in vitro in a tissue cell growth culture, and the invention also comprises a method for promoting the in vitro cultivation of mammalian tissue cells in a tissue cell culture by incorporating in the culture medium a tissue cell growth promoting amount of a peptide of formula (I).

The growth promoting activity of the peptides of formula (I) is demonstrated in the Table below. The test was carried out on cultures of human embryonic lung fibroblasts using a basal medium containing 0.67% calf serum. The test procedure was the one described by Fryklund et al. in Biochemical and Biophysical Research Communications, Vol. 61, No. 3, p. 952, (1974). The Table indicates the number of cells counted with and without addition of a peptide of the invention and the growth stimulation expressed in percent.

TABLE

| Peptide used from Example No. | Amount of Peptide μg/ml medium | Calf Serum % | No of Cells ×10$^6$ | Growth promoting activity in % above control |
|---|---|---|---|---|
| — | 0 (Control) | 0.67 | 2.45 | 0 |
| 7 | 5 | 0.67 | 3.45 | 41 |
| 8 | 5 | 0.67 | 3.80 | 55 |
| — | 0 (Control) | 0.67 | 1.70 | 0 |
| 6 | 5 | 0.67 | 2.30 | 35 |

In addition to the above mentioned use, the compounds of formula (I) also can be used as starting material for preparing higher peptides by adding additional amino acid residues.

The method of preparing the polypeptides of formula (I) is further illustrated in the following examples which are only illustrative and not intended to restrict the scope of the invention. In the Examples, all amino acids are present in their L-form unless otherwise indicated. The abbreviations used for the amino acids, peptides and protecting groups follow the recommendations of the IUPACIUB Commission on Biochemical Nomenclature (Biochemical Journal, 26, pp. 773–780, 1972).

The following abbreviations, most of which are well known and commonly used in the art, are employed herein:

| | | | |
|---|---|---|---|
| Ala = | Alanine | Gln = | Glutamine |
| Asn = | Asparagine | Glu = | Glutamic acid |
| Cys = | Cysteine | Leu = | Leucine |
| Gly = | Glycine | Pro = | Proline |
| Lys = | Lycine | Tyr = | Tyrosine |
| Phe = | Phenylalanine | Val = | Valine |
| Ser = | Serine | | |
| Thr = | Threonine | | |
| Trp = | Tryptophan | | |
| DCC = | N,N'-Dicyclohexylcarbodiimide | | |
| KO-t-Bu = | Potassium tertiary-butylate | | |
| DMF = | N,N - Dimethylformamide | | |
| TFA = | Trifluoroacetic acid | | |
| AcOAc = | Acetic acid anhydride | | |
| HOAc = | Acetic acid | | |
| Bzl = | Benzyl | | |
| Z = | Benzyloxycarbonyl | | |
| Acm = | Acetamidomethyl | | |
| ONp = | p-Nitrophenylester | | |
| Boc = | t-Butyloxycarbonyl. | | |
| Vo = | Void volume (the required volume of eluant for eluting from a gel chromatography column a substance which is totally excluded from the gel). | | |

EXAMPLE 1

Boc-Phe-Asn-Val-Asp(OBzl)-Lys(ε-2BrZ)-Lys(ε-2BrZ)-Cys(Acm)-Gln-Cys(Acm)-Asp(OBzl)-Glu(OBzl)-Leu-methylated polystyrene resin Boc-Leu (4.4 mmol) is dissolved in Me$_2$SO (20.7 ml) containing KO-t-Bu (4.0 mmol). Another portion of Me$_2$SO (20 ml) and a chloromethylated polystyrene resin (11.4 g; cross-linked with 1% divinylbenzene, available from Bio-Rad Laboratories, Richmond, California, actual capacity 1.29 mequiv./g) are added, and the slurry is stirred at 80° C. for 40 minutes. The resin is filtered off, washed in sequence in Me$_2$SO, Me$_2$So-aq. (1:1), MeOH and CH$_2$Cl$_2$, and dried. The substitution of 0.27 mmol of protected Leu per gram of resin is deduced by quantitative amino acid analysis. Thereafter 3.7 g of the Boc-Leu-polymer (equivalent to 1 mmol of Boc-Leu) is placed in the reaction vessel of a Beckman 990 peptide synthetizer. The remaining 11 amino acid moieties or residues except Boc-Gln-ONp and Boc-Asn-ONp are built up on the Boc-Leu-polymer according to the following schedule:

Schedule for coupling and re-coupling of amino acids other than active esters in solid phase synthesis (using 4 g resin)

| Step | Reagents and Operations | Mix times/ min. |
|---|---|---|
| Coupling | | |
| 1. | Dioxane wash 35 ml (3 times) | 1.5 |
| 2. | 4N HCl in Dioxane prewash 35 ml (once) | 1.5 |
| 3. | 4N HCl in Dioxane deprotection 35 ml (once) | 30 |
| 4. | Dioxane wash 35 ml (3 times) | 1.5 |
| 5. | $CH_2Cl_2$ wash 35 ml (3 times) | 1.5 |
| 6. | Triethylamine ($Et_3N$), 10% in $CH_2Cl_2$ prewash 35 ml (2 times) | 1.5 |
| 7. | Triethylamine ($Et_3N$), 10% in $CH_2Cl_2$ 35 ml | 10 |
| 8. | Boc-amino acid (2.5 × 1 mmoles) in 18 ml $CH_2Cl_2$ plus DCC 2.5 mmoles in $CH_2Cl_2$ (5.2 M) | 120 |
| 9. | $CH_2Cl_2$ wash 35 ml (2 times) | 1.5 |
| 10. | EtOH wash 35 ml (2 times) | 1.5 |
| 11. | $CH_2Cl_2$ wash 35 ml (2 times) | 1.5 |
| 12. | EtOH wash 35 ml (2 times) | 1.5 |
| Re-coupling | | |
| 1. | $CH_2Cl_2$ wash 35 ml (2 times) | 1.5 |
| 2. | DMF:$CH_2Cl_2$, 1:1 wash 35 ml (2 times) | 1.5 |
| 3. | Boc-amino acid (2.5 × 1 mmoles) in 12 ml DMF and 7 ml $CH_2Cl_2$ plus DCC 2.5 mmoles in $CH_2Cl_2$ | 120 |
| 4. | DMF:$CH_2Cl_2$ 1:1 wash 35 ml | 1.5 |
| 5. | EtOH wash 35 ml (2 times) | 1.5 |
| 6. | $CH_2Cl_2$ wash 35 ml (2 times) | 1.5 |
| 7. | EtOH wash 35 ml (2 times) | 1.5 |

The above programs for coupling and re-coupling are repeated for each of the following protected amino acids:

Boc-Phe, Boc-Val, Boc-Asp(OBzl),
Boc-Lys($\epsilon$-2BrZ), Boc-Cys(Acm) and
Boc-Glu(OBzl).

When activated esters of Boc-Asn (Boc-Asn-ONp) in position 2 of the polypeptide and of Boc-glutamine (Boc-Gln-ONp) in position 8 of the polypeptide are used, the following schedule is followed:

Schedule for Boc-Asn-ONp or for any active ester coupling and re-coupling in solid phase synthesis (using 4 g resin):

| Step | Reagents and Operations | Mix times/ min |
|---|---|---|
| Coupling: | | |
| 1. | Dioxane wash 35 ml (3 times) | 1.5 |
| 2. | 4N HCl in Dioxane prewash 35 ml | 30 |
| 3. | 4N HCl in Dioxane deprotection 35 ml | 30 |
| 4. | Dioxane wash 35 ml (3 times) | 1.5 |
| 5. | $CH_2Cl_2$ wash 35 ml (3 times) | 1.5 |
| 6. | Triethylamine ($Et_3N$) 10% in $CH_2Cl_2$ 35 ml (2 times) | 1.5 |
| 7. | Triethylamine ($Et_3N$) 10% in $CH_2Cl_2$ 35 ml | 10 |
| 8. | $CH_2Cl_2$ wash 35 ml (3 times) | 1.5 |
| 9. | DMF wash 35 ml (2 times) | 1.5 |
| 10. | Boc-Asn-ONp (5 × 1 mmole) in 9 ml DMF | 300 |
| 11. | DMF wash 35 ml (2 times) | 1.5 |
| 12. | EtOH wash 35 ml (2 times) | 1.5 |
| 13. | $CH_2Cl_2$ wash 35 ml (2 times) | 1.5 |
| 14. | EtOH wash 35 ml (2 times) | 1.5 |
| Re-coupling | | |
| 1. | $CH_2Cl_2$ wash 35 ml (3 times) | 1.5 |
| 2. | Triethylamine ($Et_3N$) 10% in $CH_2Cl_2$ prewash 35 ml | 1.5 |
| 3. | Triethylamine ($Et_3N$) 10% in $CH_2Cl_2$ 35 ml | 10 |
| 4. | $CH_2Cl_2$ wash 35 ml (3 times) | 1.5 |
| 5. | DMF wash 35 ml (2 times) | 1.5 |
| 6. | Boc-Asn-ONp (5 × 1 mmoles) in 9 ml DMF | 300 |
| 7. | DMF wash 35 ml (2 times) | 1.5 |
| 8. | EtOH wash 35 ml (2 times) | 1.5 |
| 9. | $CH_2Cl_2$ wash 35 ml (2 times) | 1.5 |
| 10. | EtOH wash 35 ml (2 times) | 1.5 |

The resulting product is that described in the title of this Example 1.

EXAMPLE 2

Boc-Cys(4MeOBzl)-Ser(Bzl)-Tyr(2BrZ)-Tyr(2BrZ)-Gln-Ser(Bzl)-Asn-Cys(4MeOBzl)-Thr(Bzl)-methylated polystyrene resin Boc-Thr(Bzl) (9.0 mmol) is dissolved in $Me_2SO$ (35ml) containing KO-t-Bu (8.1 mmol). Another portion of 100 ml $Me_2SO$ and a chloromethylated polystyrene resin cross-linked with 1% divinyl benzene (6.67 g; obtained from the aforesaid Bio-Rad; actual capacity 1.34 mequiv/g) are added. The slurry is stirred at 80° C. for 40 minutes, washed in $Me_3SO$, $Me_2SO$-aq, MeOH and $CH_2Cl_2$, and is then dried. The substitution of 0.81 mmoles of protected Thr per gram of resin is deduced by quantitative amino acid analysis. Thereafter 7.24 g of the substituted resin [equivalent to 5.86 mmoles Boc-Thr-(Bzl)] is placed in the reaction vessel of a Bechman 990 peptide synthetizer. The remaining 8 amino acid moieties or residues except Boc-Asn-ONp and Boc-Gln-ONp are built up on the Boc-Thr(Bzl)-polymer according to the following schedule:

Schedule for coupling and re-coupling of amino acids, other than active esters, in solid phase synthesis (using 8 g resin):

| Step | Reagents and Operations | Mix times/ min |
|---|---|---|
| Coupling | | |
| 1. | $CH_2Cl_2$ wash 55 ml (3 times) | 1.5 |
| 2. | 45% trifluoroacetic acid (TFA) in $CH_2Cl_2$ 55 ml | 30 |
| 3. | Step 2 repeated, deprotection | 30 |
| 4. | $CH_2Cl_2$ wash 55 ml (3 times) | 1.5 |
| 5. | 33% dioxane in $CH_2Cl_2$ 55 ml (3 times) | 1.5 |
| 6. | $CH_2Cl_2$ wash 55 ml (2 times) | 1.5 |
| 7. | Triethylamine ($Et_3N$) 10% in $CH_2Cl_2$ prewash 55 ml (2 times) | 1.5 |
| 8. | Triethylamine ($Et_3N$) 10% in $CH_2Cl_2$ neutralization 55 ml | 10 |
| 9. | $CH_2Cl_2$ wash 55 ml (4 times) | 1.5 |
| 10. | Boc-amino acid (2.5 × 1.8 mmoles) in 36 ml $CH_2Cl_2$ plus DCC 4.6 mmoles in $CH_2Cl_2$ (0.48 M) | 120 |
| 11. | $CH_2Cl_2$ wash 55 ml (2 times) | 1.5 |
| 12. | EtOH wash 55 ml (2 times) | 1.5 |
| 13. | $CH_2Cl_2$ wash 55 ml (2 times) | 1.5 |
| 14. | EtOH wash 55 ml (2 times) | 1.5 |
| Re-coupling | | |
| 1. | $CH_2Cl_2$ wash 55 ml (2 times) | 1.5 |
| 2. | DMF/$CH_2Cl_2$ 1:1 55 ml (2 times) | 1.5 |
| 3. | Boc-amino acid (2.5 × 1.8 mmoles) in 18 ml DMF and 18 ml $CH_2Cl_2$ plus DCC 4.6 mmoles in $CH_2Cl_2$ (0.48 M) | 120 |
| 4. | DMF/$CH_2Cl_2$ 1:1 55 ml | 1.5 |
| 5 | EtOH wash 55 ml (2 times) | 1.5 |
| 6. | $CH_2Cl_2$ wash 55 ml (2 times) | 1.5 |
| 7. | EtoH wash 55 ml (2 times) | 1.5 |

The above programs for coupling and re-coupling are repeated for each of the following protected amino acids:

Boc-Cys(4MeOBzl), Boc-Ser(Bzl) and
Boc-Tyr(2BrZ).

After coupling of the first Boc-Cys(4MeOBzl), an acetylation procedure is performed according to the following schedule:

| Step | Reagents and Operations | Mix times/min |
|---|---|---|
| Acetylation | | |
| 1. | CH$_2$Cl$_2$ wash 55 ml (3 times) | 1.5 |
| 2. | Triethylamine (Et$_3$N) 10% in CH$_2$Cl$_2$ 55 ml | 10 |
| 3. | CH$_2$Cl$_2$ wash 55 ml (3 times) | 1.5 |
| 4. | AcOAc in CH$_2$Cl$_2$ (1.35 M) 30 ml | 120 |
| 5. | CH$_2$Cl$_2$ wash 55 ml (2 times) | 1.5 |
| 6. | EtOH wash 55 ml (3 times) | 1.5 |
| 7. | CH$_2$Cl$_2$ wash 55 ml (2 times) | 1.5 |
| 8. | EtOH wash 55 ml (2 times) | 1.5 |
| Re-acetylation | | |
| 1. | CH$_2$Cl$_2$ wash 55 ml (2 times) | 1.5 |
| 2. | CH$_2$Cl$_2$/DMF 1:1 wash 55 ml (2 times) | 1.5 |
| 3. | AcOAc in CH$_2$Cl$_2$/DMF 1:1 (1.35M) 30 ml | 120 |
| 4. | CH$_2$Cl$_2$/DMF wash 55 ml | 1.5 |
| 5. | EtOH wash 55 ml (2 times) | 1.5 |
| 6. | CH$_2$Cl$_2$ wash 55 ml (2 times) | 1.5 |
| 7. | EtOH wash 55 ml (2 times) | 1.5 |

When activated esters of Boc-Gln and Boc-Asn in the positions 5 and 7, respectively, of the polypeptide are used, the coupling and re-coupling operations are performed according to the following schedule:

Schedule for Boc-Gln-ONp or for any active ester coupling and re-coupling in solid phase synthesis (using 8 g resin):

| Step | Reagents and Operations | Mix times/min |
|---|---|---|
| Coupling | | |
| 1. | CH$_2$Cl$_2$ wash 55 ml (3 times) | 1.5 |
| 2. | 45% TFA in CH$_2$Cl$_2$ 55 ml prewash | 1.5 |
| 3. | Step 2 repeated, deprotection | 30 |
| 4. | CH$_2$Cl$_2$ wash 55 ml (3 times) | 1.5 |
| 5. | 33% Dioxane in CH$_2$Cl$_2$ 55 ml (3 times) | 1.5 |
| 6. | CH$_2$Cl$_2$ wash 55 ml (2 times) | 1.5 |
| 7. | Triethylamine(Et$_3$N) 10% in CH$_2$Cl$_2$ prewash 55 ml (2 times) | 1.5 |
| 8. | Triethylamine (Et$_3$N) neutralization 55 ml | 10 |
| 9. | CH$_2$Cl$_2$ wash 55 ml (3 times) | 1.5 |
| 10. | DMF wash 32 ml (2 times) | 1.5 |
| 11. | Boc-Gln-ONp in 21.6 ml DMF (5 × 1.8 mmoles) | 300 |
| 12. | DMF wash 32 ml | 1.5 |
| 13. | EtOH wash 55 ml (2 times) | 1.5 |
| 14. | CH$_2$Cl$_2$ wash 55 ml (2 times) | 1.5 |
| 15. | EtOH wash 55 ml (2 times) | 1.5 |
| Re-coupling | | |
| 1 | CH$_2$Cl$_2$ wash 55 ml (3 times) | 1.5 |
| 2. | Triethylamine (Et$_3$N) 10% in CH$_2$ prewash 55 ml | 1.5 |
| 3. | Step 2 repeated 55 ml | 10 |
| 4. | CH$_2$Cl$_2$ wash 55 ml (3 times) | 1.5 |
| 5. | DMF wash 32 ml (2 times) | 1.5 |
| 6. | Boc-Gln-ONp in 21.6 ml DMF (5 × 1.8 mmoles) | 300 |
| 7. | DMF wash 32 ml (2 times) | 1.5 |
| 8. | EtOH wash 55 ml (2 times) | 1.5 |
| 9. | CH$_2$Cl$_2$ wash 55 ml (2 times) | 1.5 |
| 10. | EtOH wash 55 ml (2 times) | 1.5 |

The resulting product is that described in the title of this Example 2.

EXAMPLE 3

Cys(Acm)Tyr-Thr-Ala-Glu-Cys(Acm)-Lys-Pro-Gln-Val-Thr

Boc-Thr(Bzl) is dissolved in Me$_2$SO containing KO-t-Bu. Another portion of Me$_2$SO and a chloromethylated polystyrene resin cross-linked with 1% divinylbenzene (available from the aforesaid Bio-Rad) are added. The slurry is stirred at 80° C. for 40 minutes, washed with Me$_2$SO, Me$_2$SO-aq, and Ch$_2$Cl$_2$ and then dried. 3.0 g of the Boc-Thr(Bzl) polymer, equivalent to 2.18 mmoles of Boc-Thr(Bzl) is placed in the reaction vessel of a Beckman 990 peptide synthetiser and the remaining 10 amino acid moieties excepting the activated ester of Gln are built up on the Boc-Thr(Bzl)-polymer according to the following schedule:

Schedule for coupling and re-coupling of amino acids other than active esters in solid phase synthesis:

| Step | Reagents and Operations | Mix times/min |
|---|---|---|
| Coupling: | | |
| 1. | Dioxane wash 35 ml (3 times) | 1.5 |
| 2. | 4N HCl in Dioxane prewash 35 ml | 1.5 |
| 3. | 4N HCl in Dioxane deprotection 35 ml | 30 |
| 4. | Dioxane wash 35 ml (3 times) | 1.5 |
| 5. | CH$_2$Cl$_2$ wash 35 ml (3 times) | 1.5 |
| 6. | Triethylamine (Et$_3$N) 10% in CH$_2$Cl$_2$ prewash 35 ml (2 times) | 1.5 |
| 7. | Triethylamine (Et$_3$N) 10% in CH$_2$Cl$_2$ 35 ml | 10 |
| 8. | Boc-amino acid (2.5 × 1 mmoles in 18 ml CH$_2$Cl$_2$ plus DCC 2.5 mmoles in CH$_2$Cl$_2$ (0.5 M) | 120 |
| 9. | CH$_2$Cl$_2$ wash 35 ml (2 times) | 1.5 |
| 10. | EtHO wash 35 ml (2 times) | 1.5 |
| 11. | CH$_2$Cl$_2$ wash 35 ml (2 times) | 1.5 |
| 12. | EtOH wash 35 ml (2 times) | 1.5 |
| Re-coupling | | |
| 1. | CH$_2$Cl$_2$ wash 35 ml (2 times) | 1.5 |
| 2. | DMF:CH$_2$Cl$_2$ 1:1 wash 35 ml (2 times) | 1.5 |
| 3. | Boc-amino acid (2.5 × 1 mmoles) in 12 ml DMF and 7 ml CH$_2$Cl$_2$ | 120 |
| 4. | DMF:CH$_2$Cl$_2$ 1:1 wash 35 ml | 1.5 |
| 5. | EtOH wash 35 ml (2 times) | 1.5 |
| 6. | CH$_2$Cl$_2$ wash 35 ml (2 times) | 1.5 |
| 7. | EtOH wash 35 ml (2 times) | 1.5 |

The cycle of steps 1 to 12 plus re-coupling steps 1 to 7 is repeated with each of the following blocked amino acids in building up the peptide chain:

Boc-Val, Boc-Pro, Boc-Lys($\epsilon$-2BrZ),
Boc-Cys(Acm), Boc-Glu(Bzl) and Boc-Tyr(Bzl).

After the introduction of Boc-Val, an acetylation step is carried out according to the following schedule:

| Step | Reagents and Operations | Mix times/min |
|---|---|---|
| Acetylation | | |
| 1. | CH$_2$Cl$_2$ wash 35 ml (3 times) | 1.5 |
| 2. | Triethylamine (Et$_3$N) 10% in CH$_2$Cl$_2$ 35 ml | 10 |
| 3. | CH$_2$Cl$_2$ wash 35 ml (3 times) | 1.5 |
| 4. | AcOAc in CH$_2$Cl$_2$ (0.43 M) 46 ml | 120 |
| 5. | CH$_2$Cl$_2$ wash 35 ml (2 times) | 1.5 |
| 6. | EtOH wash 35 ml (3 times) | 1.5 |
| 7. | CH$_2$Cl$_2$ wash 35 ml (2 times) | 1.5 |
| 8. | EtOH wash 35 ml (2 times) | 1.5 |
| Re-acetylation | | |
| 1. | CH$_2$Cl$_2$ wash 35 ml (2 times) | 1.5 |
| 2. | CH$_2$Cl$_2$/DMF 1:1 wash 35 ml (2 times) | 1.5 |
| 3. | AcOAc in CH$_2$Cl$_2$/DMF 1:1 (0.43 M) 46 ml | 120 |
| 4. | CH$_2$Cl$_2$DMF wash 35 ml | 1.5 |
| 5. | EtOH wash 35 ml (2 times) | 1.5 |

-continued

| Step | Reagents and Operations | Mix times/min |
|---|---|---|
| 6. | $CH_2Cl_2$ wash 35 ml (2 times) | 1.5 |
| 7. | EtOH wash 35 ml (2 times) | 1.5 |

When an activated ester of Boc-Gln is introduced in the position 9 of the polypeptide, the following schedule is used:

Schedule for Boc-Gln-ONp or for any active ester coupling and re-coupling in solid phase synthesis:

| Step | Reagents and Operations | Mix times/min |
|---|---|---|
| Coupling | | |
| 1. | Dioxane wash 35 ml (3 times) | 1.5 |
| 2. | 4N in Dioxane prewash 35 ml | 30 |
| 3. | 4N in Dioxane deprotection 35 ml | 30 |
| 4. | Dioxane wash 35 ml (3 times) | 1.5 |
| 5. | $CH_2Cl_2$ wash 35 ml (3 times) | 1.5 |
| 6. | Triethylamine ($Et_3N$) 10% in $CH_2Cl_2$ 35 ml (2 times) | 1.5 |
| 7. | Triethylamine ($Et_3N$) 10% in $CH_2Cl_2$ 35 ml | 10 |
| 8. | $CH_2Cl_2$ wash 35 ml (3 times) | 1.5 |
| 9. | DMF wash 35 ml (2 times) | 1.5 |
| 10. | Boc-Gln-ONp (50 × 1 mmole) in 15 ml DMF | 300 |
| 11. | DMF wash 35 ml (2 times) | 1.5 |
| 12. | EtOH wash 35 ml (2 times) | 1.5 |
| 13. | $CH_2Cl_2$ wash 35 ml (2 times) | 1.5 |
| 14. | EtOH wash 35 ml (2 times) | 1.5 |
| Re-coupling | | |
| 1. | $CH_2Cl_2$ wash 35 ml (3 times) | 1.5 |
| 2. | Triethylamine($Et_3N$) 10% in $CH_2Cl_2$ prewash 35 ml | 1.5 |
| 3. | Triethylamine ($Et_3N$) 10 % in $CH_2Cl_2$ 35 ml | 10 |
| 4. | $CH_2Cl_2$ wash 35 ml (3 times) | 1.5 |
| 5. | DMF wash 35 ml (2 times) | 1.5 |
| 6. | Boc-Gln-ONp (50 × 1 mmole) in 15 ml DMF | 300 |
| 7. | DMF wash 35 ml (2 times) | 1.5 |
| 8. | EtOH wash 35 ml (2 times) | 1.5 |
| 9. | $CH_2Cl_2$ wash 35 ml (2 times) | 1.5 |
| 10. | EtOH wash 35 ml (2 times) | 1.5 |

The dry weight of the solid fully protected undecapeptide polymer adduct is 6.2 g. The product (6.2 g) is then treated with liquid hydrogen fluoride (75 ml) at 0° C. for 1 hour in the presence of anisole (13 ml). After removal of the HF and the anisole, and drying, all under vacuum, for 24 hours, the polymer is washed with ethyl acetate (6×25 ml) to remove any residual anisole. The crude product is extracted with 0.2 M acetic acid (5×25 ml) and the combined extract is evaporated and lyophilized (2.56 g). The above mentioned crude product is purified by gel filtration as follows: 2.56 g of the product in 10 ml of 0.2 M acetic acid is applied to a column (6.5 cm in diameter and 115 cm in height) of 40 to 120 beads of the SEPHADEX G-15 which is a fraction of dextran, an anhydroglucose polymer, cross-linked with epichlorohydrin (product of Pharmacia Fine Chemicals, Uppsala, Sweden, and of Piscatawny, New Jersey, U.S.A.) showing a water regain value of 2.5 to 3.5 ml bed volume/gram dry SEPHADEX G-15 and with the capacity to fractionate peptides with a molecular weight less than 1500. The column is previously equilibrated with 0.2 M acetic acid, and the crude product is eluted with the said solvent. Fractions of 15 ml each are collected. The elution pattern observed at 281 nm showed three peaks with the major peak centered at 1.7 Vo (1.2 g). In order to oxidize any cysteine residues which have been deblocked during the treatment with HF, the product is treated with $K_3Fe(CN)_6$ (8 ml; 0.01 M, 20 minutes) and an anion exchange resin (Bio-Rad AG 3 beads (product of the aforesaid Bio-Rad)) a weakly basic epoxy amine type anion exchange resin (100 to 200 mesh), chloride form, having the formula $\phi$-$CH_2N^+H(R_2)Cl^-$ with predominantly tertiary amino functional groups and R being methyl or ethyl) and again purified by gel filtration as described above. Fractions of 7.5 ml each are collected and the tubes 76–83, which are Pauly positive, are collected and lyophilized. (425 mg.)

EXAMPLE 4

Phe-Asn-Val-Asp-Lys-Lys-Cys(Acm)-Gln-Cys(Acm)-Asp-Glu-Leu

The product (i.e., the peptide polystyrene resin adduct) obtained in Example 1 is treated in vacuo with liquid hydrogen fluoride (70 ml) and anisole (31 ml) at 0° C. for 1 hour. The hydrogen fluoride and anisole then are removed as quickly as possible under reduced pressure. The residue is dried under vacuum for 24 hours and then washed with ethyl acetate to remove any residual anisole. The crude peptide product is extracted from the polymer with 0.2 M HOAc (5×25 ml) and then is lyophilized, then purified and characterized as follows: The product in a small volume of 0.2 M HOAc is applied to a column (6.5×92 cm) of SEPHADEX G-15 beads (Pharmacia Fine Chemicals), equilibrated in 0.2 M HOAc, Vo=1140 ml. The effluent is analyzed by UV light at 280 nm. The fractions corresponding to 1.3 to 1.6 Vo are collected, combined and freeze-dried. The peptide then is applied in 0.1 pyridine-acetic acid buffer, pH 5.0, to an ion-exchange column of 100 to 200 mesh beads of the DOWEX 50WX2 which is the H-form strong cation exchange resin chlorosulfonated copolymer of styrene cross-linked with 2% of divinyl benzene (product of Dow Chemical Company, of Midland, Michigan) showing a total wet volume exchange capacity of a minimum of 0.6 milliequivalents per millimeter and a minimum water retention capacity of 74 to 82%. The column is eluted by a stepwise increasing pH gradient, pH 5.0 to pH 7.5. Fractions of 5 ml are collected and analyzed by ninhydrin spot tests. Two major components are eluted, one at pH 5.5 and one at pH 7.5. The two products are lyophilized and analyzed by thin layer chromatography and isotachophoresis. The compound eluted at pH 7.5 is then chromatographed in 0.05 M ammonium acetate, pH 5.9, on an ion exchange column (2.5×20 cm) of 40 to 120μ beads of the CM-SEPHADEX C-25 which is the sodium form weak cation exchange resin of dextran, an anhydroglucose polymer, cross-linked with epichlorohydrin and with its functional carboxymethyl groups attached by ether linkages to the glucose of the dextran chains (product of Pharmacia Chemicals Uppsala, Sweden, and of Piscatawny, New Jersey). Three peaks are eluted according to UV absorption at 280 nm and 230 nm. The last one of these is pooled, freeze-dried, desalted on a column of 50 to 150μ beads of the SEPHADEX G 25 which is a fraction of dextran, an anhydroglucose polymer, cross-linked with epichlorohydrin (a product of the aforesaid Pharmacia Fine Chemicals) showing a water regain value of 4 to 6 ml bed volume/gram dry SEPHADEX G-25, with the capacity to fractionate peptides and globular proteins with a molecular weight of 1000 to 5000. The column of SEPHADEX G-25 is previously equilibrated with 0.2 M HOAc, and after desalting on this column, the peptide is freeze-dried again.

The purified peptide is analyzed by thin layer chromatography (SiO$_2$) and isotachophoresis. Thin layer chromatography in EtOAc/pyridine/HOAc/H$_2$O (5:5:1:3) gives one single spot, Rf=0.7; in CHCl$_3$/MeOH/17% NH$_3$ (20:20:9), Rf=0.3.

Isotachophoresis is performed in a system where the leading electrolyte consists of 0.01 M HCl and 0.02 M amediol (i.e. 2-amino-2-methyl-1,3-propandiol) in 0.5% hydroxypropylmethyl cellulose and the terminating electrolyte is 0.01 M ε-aminocaproic acid with Ba(OH$_2$) added to pH 10. In this system, the relative step height corresponding to the purified peptide is 0.57. The purity of the peptide was assessed to 75 to 80%.

EXAMPLE 5

Cys-Ser-Tyr-Tyr-Gln-Ser-Asn-Cys-Thr

The product obtained in Example 2, to separate the polypeptide from its adduct with the polymer, is treated under vacuum with liquid hydrogen fluoride (50 ml) and anisole (7 ml) at 0° C. for 1 hour. The hydrogen fluoride and anisole are removed under reduced pressure and the residue is dried under vacuum for 18 hours and washed with ethyl acetate (5×15 ml) to remove any residual anisole. The product is then taken up in acetic acid containing mercaptoethanol (0.015 M), filtered off from the resin and lyophilized (0.96 g).

The crude product, is dissolved in a small volume of 0.2 M acetic acid and 0.015 M mercaptoethanol and applied to a column (2.6 cm in diameter and 100 cm in height) with a bed of SEPHADEX G-15 previously equilibrated with 0.2 M acetic acid and 0.015 M mercaptoethanol. The column is eluted with that solvent and sequential fractions of 5 ml each are collected. The column effluent is monitored by spectrophotometric measurements at 281 nm and five peptide containing fractions (A-E) are obtained. Fraction C, in combined tubes 105 to 146, yielding 72.3 mg, are the purest as indicated by thin layer chromatography, and contain the peptide of the title of this Example 5.

EXAMPLE 6

Cys-Tyr-Thr-Ala-Glu-Cys-Lys-Pro-Gln-Val-Thr

The product obtained in Example 3 is treated with a solution of Hg(OAc)$_2$ in water (93 mg/2000 ml) for 2 hours. The pH of the solution is adjusted by 0.2 M acetic acid to 4.0. The product is then treated with H$_2$S, the precipitate of HgS is filtered off and the pH is adjusted to 7 with NH$_4$OH. The peptide (100 mg/l) is then oxidized by air for 2 days. After concentration to a small volume, the crude cyclic undecapeptide is purified by gel filtration on a SEPHADEX G-15 (of the aforesaid Pharmacia Fine Chemicals) beads column (6.5 cm in diameter and 115 cm in height) using 0.2 M HOAc as the eluent, and sequential fractions of 1 ml each are taken and tubes 39 to 71 are collected (Pauly positive) and lyophilized (62 mg).

Thin layer chromatography of the resulting cyclic form of the starting undecapeptide in n-butanol/aq/-HOAc/ethyl acetate (1:1:1:1), SiO$_2$, gives one single spot Rf=0.3, positive to ninhydrin and Pauly reagents. Amino acid analysis after hydrolysis in 6 N HCl for 24 hours gives the following amino acid ratios (the numbers within brackets are the theoretical values):

Ala 1.00(1); Cys 2.2 (2); Glu 2.0 (2); Lys 1.0 (1); Pro 1.2 (1); Thr 1.9 (2); Tyr 1.0 (1); Val 0.8 (1).

EXAMPLE 7

Phe-Asn-Val-Asp-Lys-Lys-Cys-Gln-Cys-Asp-Glu-Leu 93 mg of the linear dodecapeptide product obtained in Example 4 is dissolved in 176 ml 67% HOAc and added within 10 minutes under vigorous stirring to 64 ml 0.05 M I$_2$ i HOAc and 16 ml H$_2$O. After another 25 minutes, the reaction is stopped by adding 9 ml 0.5 M NaAc and 0.5 M Na$_2$S$_2$O$_3$ until only a faintly yellow colour remains. Most of the water is evaporated at 40 mm Hg and 30° to 35° C. The concentrate is chromatographed on a column of SEPHADEX G-15 (product of the aforesaid Pharmacia Fine Chemicals) beads in 0.2 M HOAc. The void volume of the column is 136 ml and the peptide is eluted at 1.3 to 1.7 Vo. The mixture is further purified by preparative electrophoresis on a column (1 cm in diameter and 100 cm in height) with a bed of cellulose powder (Munktell 410), in 0.05 M pyridinium acetate, pH=5.0; migration towards the anode, 7 mA, 1000 V, 20 hours. The main fraction is collected.

Analysis of the final product (of the title of this Example 7) was performed. TLC in EtOAc/pyridine/-HOAc/H$_2$O (5:5:1:3), Rf=0.7; CHCl$_3$/MeOH/17% NH$_3$ (20:20:9), Rf=0.4. The relative step height measured in isotachophoresis was 0.19. Amino acid analysis:

Asp 3.1 (3); Glu 1.7 (2); Cys 2.0 (2); Val 1.0 (1); Phe 1.0 (1), Lys 2.2 (2).

EXAMPLE 8

Cys-Ser-Tyr-Tyr-Gln-Ser-Asn-Cys-Thr:

The reduced linear nonapeptide product of Example 5 is dissolved in 0.0005 M NH$_4$OAc (1400 ml; pH 7.0). The solution is titrated dropwise with stirring with 0.01 M potassium ferricyanide solution until a permanent yellow colour is observed (14.5 ml). The solution to 5.0 with acetic acid. Bio-Rad AG-3 beads (product of the aforesaid Bio-Rad Laboratories), a weakly basic epoxyamine type anion exchange resin (100 to 200 mesh), chloride form, having the formula φ-CH$_2$N+HR$_2$)Cl$^-$ with predominately tertiary amine functional groups and R being methyl or ethyl, (4 g), is added and the turbid solution is stirred for 15 minutes. The solution is filtered over diatomaceous earth filter aid and then evaporated. The oxidized peptide is then purified, first by gel filtration in the same manner as described above and then by preparative electrophoresis on a column (1 cm in diameter and 100 cm in height) with a bed of cellulose powder previously equilibrated with formic acid (2.5%) and acetic acid (7.8%). The electrophoresis is performed with 5 mA, 1000 V for 18 hours. The elution pattern, observed at 281 nm, showed a symmetrical peak having a maximum at 0.3 Vo from the starting point towards the cathode. The product is lyophilized and finally dissolved in a small volume of the upper phase of n-butanol/water/acetic acid (4:5:1) and is applied to a column (1 cm in diameter and 65 cm in height) with a bed of SEPHADEX G-25 beads (product of the aforesaid Pharmacia Fine Chemicals) previously equilibrated with the lower phase of the said system and then with the upper phase. The column is eluted with the upper phase, and fraction 132 to 165 of 0.6 are collected. The fraction is homogeneous on thin layer chromatography, system (1:1:1:1) (n-butanol/ethylacetate/acetic acid/water) and by isotachophoresis (relative step height 0.39).

The end product is the cyclic nonapeptide of the title of this Example 8.

After hydrolysis of the peptide for 24 hours in 6 M HCl at 110° C. in an evacuated sealed tube, the following amino acid analysis values are obtained:

Asp 1.0 (1); Glu 1.0 (1); Ser 1.9 (2); Thr 1.0 (1); Tyr 1.9 (2).

While the peptides of the invention are illustrated by the eight specific peptides of Example 1 through 8, any one peptide embraced by the formula (I) in the first paragraph of this specification can be prepared starting with a single amino acid or combinations with a lower peptide such as a dipeptide, or tripeptide, or tetrapeptide, which then is combined by the pertinent combination of steps such as indicated in the various Examples 1 to 8, to provide any other desired peptide embraced by formula (I). All such other peptides are to be considered as set forth herein as prepared by the pertinent combination of steps to provide them, as if each of them was written out in full as resulting with its specific example written out in full herein.

While the invention has been explained in detailed description of certain specific embodiments of it, it is understood that various modifications and substitutions may be made in any of the specific examples within the scope of the appended claims which are intended to embrace equivalents of them.

We claim:

1. A growth promoting polypeptide having the general formula

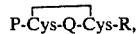

and the corresponding linear form thereof, wherein
P is hydrogen, or Phe-Asn-Val-Asp-Lys-Lys-;
Q is selected from -Gln, or -Ser-Tyr-Tyr-Gln-Ser-Asn-, or -Tyr-Thr-Ala-Glu-; and
R is selected from -Thr, or -Lys-Pro -Gln-Val-Thr-, or -Asp-Glu-Leu-;
and the corresponding peptide in which its reactive groups are projected in any of Asp, Cys, Glu, Lys, Ser, Thr, Tyr, Which are included; as well as the corresponding pharmaceutically acceptable acid addition salts of each said peptide.

2. A polypeptide as claimed in claim 1, which is Boc-Phe-Asn-Val-Asp(OBzl)-Lys(ε-2Brz)-Lys (ε-2Brz)-Cys(Acm)-Gln-Cys(Acm)-Asp(OBzl)-glu(OBzl)-Leu; and the correspondiing linear form, as well as its corresponding pharmaceutically acceptable acid addition salts.

3. A polypeptide as claimed in claim 1, which is Boc-Cys(4MeOBzl)-Ser(Bzl)-Tyr(2BrZ)-Tyr(2BrZ)-Gln-Ser(Bzl)-Asn-Cys(4MeOBzl)-Thr(Bzl); and the corresponding linear form, as well as its corresponding pharmaceutically acceptable acid addition salts.

4. A polypeptide as claimed in claim 1, which is Cys-(Acm)-Tyr-Thr-Ala-Glu-Cys (Acm)-Lys-Pro-Gln-Val-Thr; and the corresponding linear form, as well as its corresponding pharmaceutically acceptable acid addition salts.

5. A polypeptide as claimed in claim 1, which is Phe-Asn-Val-Asp-Lys-Cys(Acm)-Gln-Cys(Acm)-Asp-Glu-Leu; and the corresponding linear form, as well as its corresponding pharmaceutically acceptable acid addition salts.

6. A polypeptide as claimed in claim 1, which is Cys-Ser-Tyr-Tyr-Gln-Ser-Asn-Cys-Thr; and the corresponding linear form, as well as its corresponding pharmaceutically acceptable acid addition salts.

7. A polypeptide as claimed in claim 1, which is Cys-Tyr-Thr-Ala-Glu-Cys-Lys-Pro-Gln-Val-Thr; and the corresponding linear form, as well as its corresponding pharmaceutically acceptable acid addition salts.

8. A polypeptide as claimed in claim 1, which is Phe-Asn-Val-Asp-Lys-Lys-Cys-Gln-Cys-Asp-Glu-Leu; and the corresponding linear form, as well as its corresponding pharmaceutically acceptable acid addition salts.

9. A method of promoting the cell production in the in vitro cultivation of mammalian tissue cells in a tissue cell culture medium, which comprises the step of incorporating in the culture medium a cell growth promoting content of a member of the class of the polypeptides as claimed in claim 1.

* * * * *